(12) United States Patent
Mihara et al.

(10) Patent No.: US 9,395,382 B2
(45) Date of Patent: Jul. 19, 2016

(54) SPECIMEN ANALYZING APPARATUS

(71) Applicant: Sysmex Corporation, Kobe-shi, Hyogo (JP)

(72) Inventors: Takahito Mihara, Kobe (JP); Takaaki Nagai, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 0 days.

(21) Appl. No.: 14/189,654

(22) Filed: Feb. 25, 2014

(65) Prior Publication Data

US 2014/0242706 A1    Aug. 28, 2014

(30) Foreign Application Priority Data

Feb. 28, 2013    (JP) .................. 2013-038707

(51) Int. Cl.
*G01N 35/00*    (2006.01)
*G01N 35/10*    (2006.01)
*G01N 35/04*    (2006.01)

(52) U.S. Cl.
CPC .... *G01N 35/1004* (2013.01); *G01N 2035/0412* (2013.01); *Y10T 436/114998* (2015.01)

(58) Field of Classification Search
CPC ............ G01N 35/00722; G01N 35/00; G01N 35/0092; G01N 358/0095; G01N 35/00584; G01N 2035/0415; G01N 2035/00742; G01N 2035/00851; Y10T 436/11; Y10T 436/113332; Y10T 436/114165; Y10T 436/114998; Y10T 436/00

USPC ................................... 436/49, 47, 43
See application file for complete search history.

(56) References Cited

U.S. PATENT DOCUMENTS

| | | | |
|---|---|---|---|
| 4,817,443 A | 4/1989 | Champseix et al. | |
| 5,592,959 A | 1/1997 | Nagai | |
| 2003/0070498 A1 * | 4/2003 | Ohyama et al. | 73/863.01 |
| 2010/0282003 A1 * | 11/2010 | Hamada et al. | 73/863.91 |

FOREIGN PATENT DOCUMENTS

| | | |
|---|---|---|
| JP | 08-004617 Y2 | 2/1996 |
| JP | 11-108923 A | 4/1999 |

* cited by examiner

*Primary Examiner* — Christine T Mui
(74) *Attorney, Agent, or Firm* — Brinks Gilson & Lione

(57) ABSTRACT

To provide a specimen analyzing apparatus capable of preventing a reduction in analysis accuracy caused by contamination of a measurement sample by a substance attached to a cleaning unit, the present invention provides a blood analyzer 100 which includes a cleaning unit 7 for cleaning an aspirating tube 1 positioned within a through-hole 72, a vertical moving unit 5 for moving the aspirating tube 1 along a through-hole relative to the cleaning unit 7, and a blade 8 for removing a substance attached to the outer side of the cleaning unit 7, wherein an aspirating tube 1 is provided for aspirating a sample, a through-hole 72 is formed to allow the aspirating tube 1 to pass therethrough, and a supply path 73 is formed for supplying a cleaning liquid to the through-hole 72.

17 Claims, 6 Drawing Sheets

BLADE REMOVAL (FIRST EMBODIMENT)

VIEW FROM BELOW THE CLEANING UNIT (FIRST EMBODIMENT)

AIR SUCTION (SECOND EMBODIMENT)

SUBSTANCE REMOVAL PROCESS (SECOND EMBODIMENT)

AIR INJECTION (FIRST MODIFICATION)

LIQUID INJECTION (SECOND MODIFICATION)

_US 9,395,382 B2_

SPECIMEN ANALYZING APPARATUS

RELATED APPLICATIONS

This application claims priority under 35 U.S.C. §119 to Japanese Patent Application No. 2013-038707 filed on Feb. 28, 2013, the entire content of which is hereby incorporated by reference.

FIELD OF THE INVENTION

The present invention relates to a specimen analyzing apparatus, and specifically relates to a specimen analyzing apparatus provided with a cleaning unit for cleaning an aspirating tube.

BACKGROUND OF THE INVENTION

There are well known conventional cleaning devices provided with cleaning units for cleaning aspirating tubes (for example, U.S. Pat. No. 4,817,443).

U.S. Pat. No. 4,817,443 discloses a cleaning device provided with a needle for aspirating and holding a sample such as blood, and a cylindrical chamber having a through-hole through which the needles passes, and further provided with a cleaning case for cleaning the needle positioned within the cylindrical chamber. The cleaning device is configured to move the needle relative to the cleaning case along the through-hole of the cylindrical chamber. An end piece for reducing the inner diameter of the cylindrical chamber to prevent the cleaning liquid from flowing out into the cylindrical chamber, is mounted on the bottom end of the cylindrical chamber so that the bottom surface of the end piece and the bottom surface of the cylindrical chamber are on the same plane.

The conventional cleaning device disclosed in U.S. Pat. No. 4,817,443 is configured clean the aspirating tube in the through-hole of the cleaning unit after a sample such as blood has been aspirated, and subsequently the sample is analyzed by an analyzing unit.

However, this conventional cleaning device may not produce accurate analysis results when the aspirating tube is cleaned after the sample has been aspirated by the aspirating tube and the sample is subsequently analyzed.

SUMMARY OF THE INVENTION

The scope of the present invention is defined solely by the appended claims, and is not affected to any degree by the statements within this summary.

A first aspect of the present invention is a specimen analyzing apparatus, comprising:
  an aspirating tube configured to aspirate a specimen;
  a detecting unit configured to measure the specimen aspirated by the aspirating unit;
  a cleaning unit, in which a through-hole for passing the aspirating tube and a supplying path for supplying a cleaning solution into the through-hole are formed, configured to clean the aspirating tube positioned in the through-hole;
  a first moving unit configured to change a relative position of the aspirating tube and the cleaning unit with the aspirating tube being passing through the through-hole; and
  a removing unit configured to remove a substance attached on the outer side of the cleaning unit.

A second aspect of the present invention is a specimen analyzing apparatus, comprising:
  an aspirating tube configured to aspirate a specimen;
  a detecting unit configured to measure the specimen aspirated by the aspirating unit;
  a cleaning unit, in which a through-hole for passing the aspirating tube and a supplying path for supplying a cleaning solution into the through-hole are formed, configured to clean the aspirating tube positioned in the through-hole;
  a first moving unit configured to move the aspirating tube relative to the cleaning unit through the through-hole; and
  a removing unit configured to remove a substance attached on the outer side of the cleaning unit.

A third aspect of the present invention is a specimen analyzing method comprising:
  aspirating a specimen by using an aspirating tube;
  cleaning the aspirating tube positioned in a through-hole of a cleaning unit, in which the through-hole for passing the aspirating tube and a supplying path for supplying a cleaning solution into the through-hole are formed, while changing a relative position of the aspirating tube and the cleaning unit; and
  removing a substance attached on outer side of the cleaning unit.

DETAILED DESCRIPTION OF THE PREFERRED EMBODIMENTS

The preferred embodiments of the present invention will be described hereinafter with reference to the drawings.

The embodiments of the present invention are described below based on the drawings.

First Embodiment

The structure of the blood analyzer 100 of the first embodiment of the present invention is described below with reference to FIGS. 1 through 4.

Figure 1:
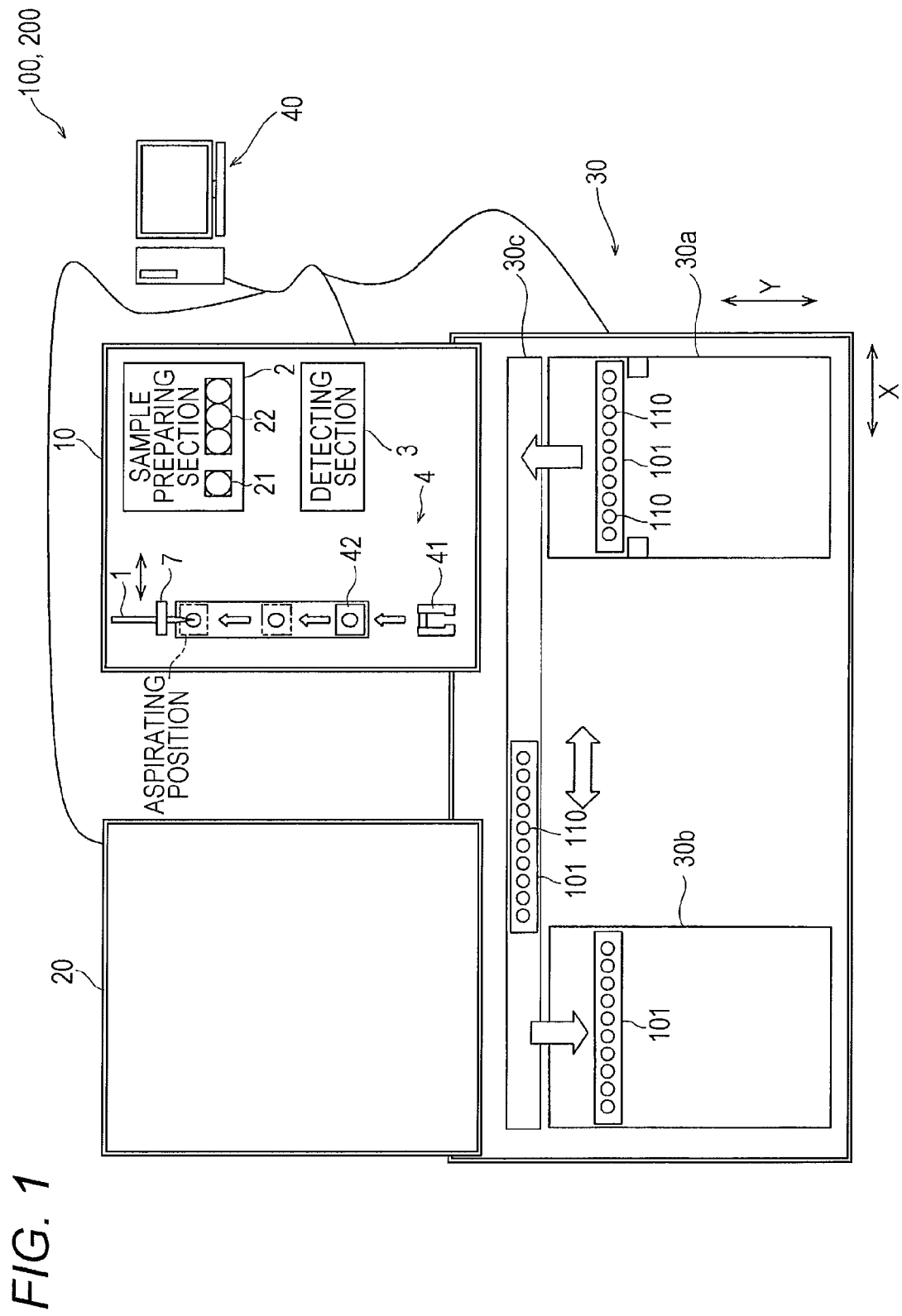
FIG. 1 is a brief plan view showing the structure of a blood analyzer of the first and second embodiments of the present invention.

The blood analyzer 100 has mutually identical first measuring unit 10 and second measuring unit 20, sample transporting device 30 arranged on the front sides of the first measuring unit 10 and the second measuring unit 20, and a control device 40 configured by a PC (personal computer) electrically connected to the first measuring unit 10, second measuring unit 20, and sample transporting device 30, as shown in FIG. 1.

The first measuring unit 10 is configured by an aspirating tube 1 for aspirating and holding blood sample from a sample container 110, sample preparing section 2 for preparing a measurement sample (specimen) from blood aspirated by the aspirating tube 1, and detecting section 3 measuring and examining the measurement sample prepared by the sample preparing section 2. The first measuring unit 10 also has a sample container transporting section 4 for receiving into the first measuring unit 10 the sample container 110 held in a rack 101 transported by the sample transporting section 30, and transporting the sample container 110 to the aspirating position of the aspirating tube 1.

Figure 2:
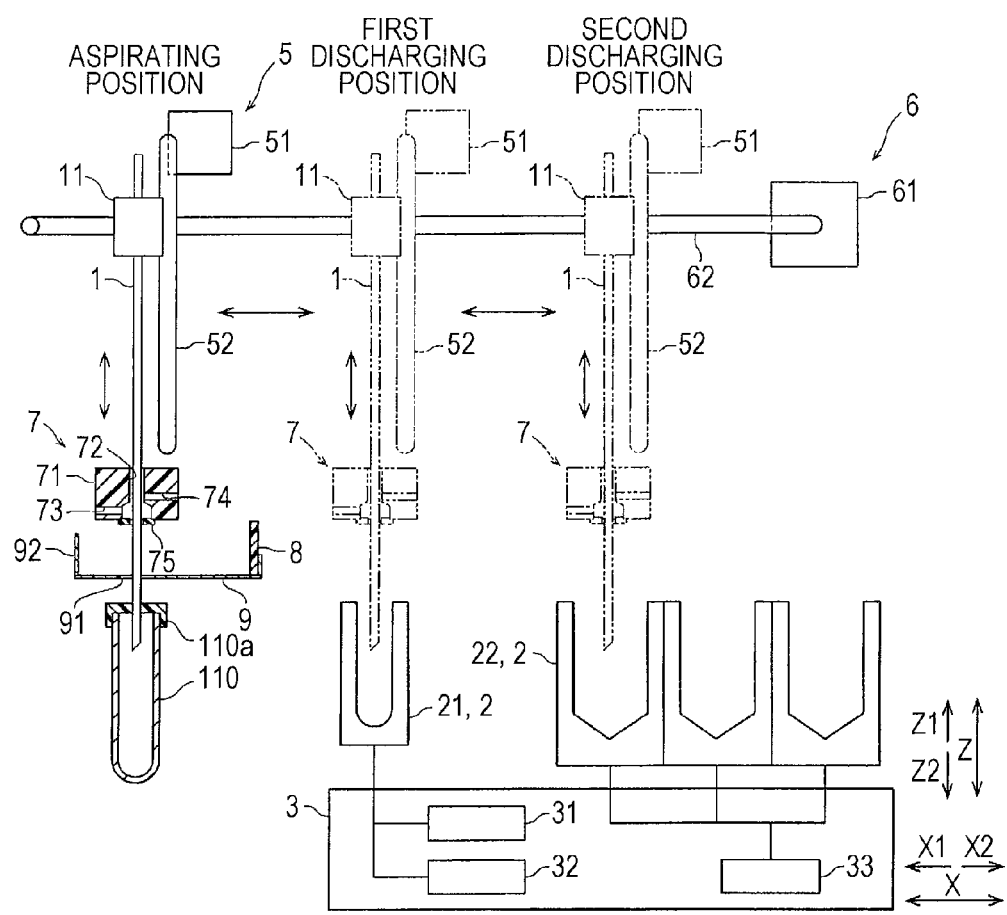
FIG. 2 briefly illustrates the structures of the aspirating tube and cleaning unit of the blood analyzer of the first embodiment.

The tip of the aspirating tube 1 is needle-like so as to pass through the cap 110a of the sealed sample container 110. As shown in FIG. 2, the aspirating tube 1 is configured to be movable both vertically (Z direction) and horizontally (X direction). Specifically, a vertical moving unit 5 for moving the aspirating tube 1 vertically, and a horizontal moving unit 6 for moving the aspirating tube 1 horizontally are provided within the first measuring unit 10.

The sample preparing section 2 includes a first chamber 21 and a second chamber 22, and is configured to prepare a measurement sample from the blood aspirated by the aspirating tube 1. Specifically, the first chamber 21 is configured to prepare a measurement sample to measure RBC and HGB. The measurement sample prepared in the first chamber 21 is respectively sent to the RBC detecting unit (DC detecting unit) 31 and HGB detecting unit (light absorbance detecting unit) 32 of the detecting section 3. The second chamber 22 has three containers. Measurement samples for white blood cell detection, reticulocyte detection, and platelet detection are prepared in these three containers. The measurement samples prepared in the second chamber 22 are sent to the FCM (flow cytometry) detecting unit of the detecting section 3.

The detecting section 3 includes an RBC detecting unit (DC detecting unit) 31 for detecting RBC (red blood cell detection) via the sheath flow-DC method, HGB detecting unit (light absorbance detection) 32 for HGB detection (detection of hemoglobin in the blood), and FCM detecting unit 33 for measuring white blood cells, reticulocytes and platelets via flow cytometry.

The sample container transporting section 4 includes a hand unit 41 capable of gripping the sample container 110, and a sample container moving unit 42 for moving, in the Y direction, the sample container 110 retrieved from the rack 101 by the hand unit 41 at the aspirating position of the aspirating tube 1, as shown in FIG. 1.

The vertical moving unit 5 includes a motor 51, and a drive belt 52 extending vertically and configured to rotate via the motor 51, as shown in FIG. 2. The aspirating tube 1 is mounted on the drive belt 52 by means of a mounting member which is not shown in the drawing. The aspirating tube 1 is configured to move vertically via the rotation of the drive belt 52. The aspirating tube 1 is lowered by the vertical moving unit 5 and aspirates blood within the sample container 110 through the cap 110a of the sample container 110 which has been transported to the aspirating position when aspirating blood from the sample container 110 placed at the aspirating position. After aspirating the blood, the aspirating tube 1 is lifted by the vertical moving unit 5 and returned to a predetermined position.

The horizontal moving unit 6 includes a motor 61, and a drive belt 62 extending horizontally and configured to rotate via the motor 61. An aspirating tube 1 is mounted on the drive belt 62 by means of a mounting member 11. The aspirating tube 1 is configured to move horizontally via the rotation of the drive belt 62. The aspirating tube 1 sequentially moves to positions corresponding to the first chamber 21 and the second chamber 22 of the sample preparing section 2 by moving horizontally from the aspirating position via the horizontal moving unit 6. The aspirating tube 1 discharges the aspirated blood into the first chamber 21 at the first discharging position corresponding to the first chamber 21. The aspirating tube 1 discharges the aspirated blood into the second chamber 22 at the second discharging position corresponding to the second chamber 22. The aspirating tube 1 discharges blood at the first and second discharging positions when lowered to a predetermined position by the downward movement of the vertical moving unit 5. The aspirating position and the first and second discharging positions are arranged linearly in planar view.

Figure 3:
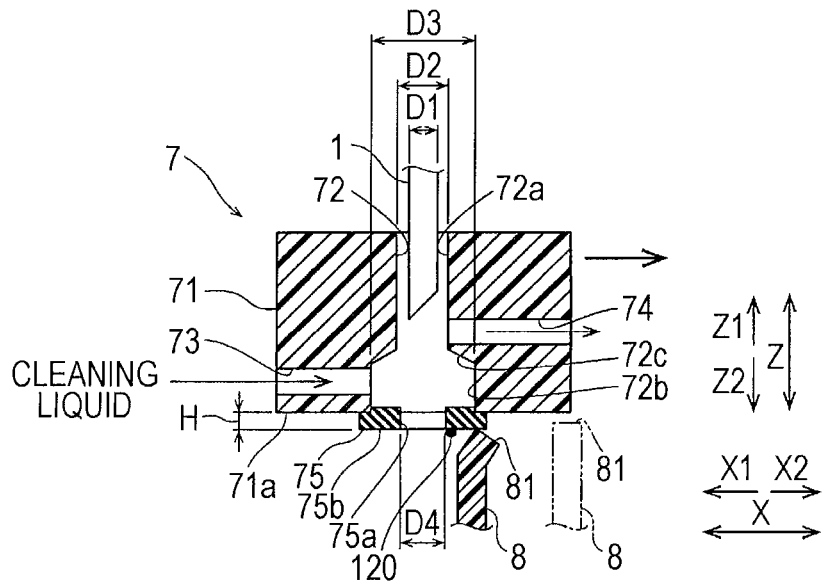
FIG. 3 is an enlarged cross sectional view of the cleaning unit and blade shown in FIG. 2.

As shown in FIGS. 2 and 3, the blood analyzer 100 also has a cleaning unit 7 for cleaning the aspirating tube 1, and a blade 8 for removing a substance 120 attached to the outside part at the bottom of the cleaning unit 7. The present inventors discovered that when the cleaning the aspirating tube 1 while relatively moving the aspirating tube 1 through the through-hole 72 in an apparatus provided with an aspirating tube 1 and a cleaning unit 7 such as the blood analyzer 100, clotted blood and debris from the cap 110a attached to the top part of the cap 110a of the sample container 110 will adhere to the outer surface of the aspirating tube 1 as foreign substances, and this substance 120 may move in conjunction with the lifting of the aspirating tube 1 so as to adhere to the bottom part of the cleaning unit 7. The present inventors discovered that the substance 120 attached to the outer side of the bottom of the cleaning unit 7 may fall and contaminate the measurement sample prepared by the sample preparing section 2, thus reducing detection accuracy. As a result of intensive study, the present inventors devised a structure to eliminate this problem by providing a removing unit to remove the substance 120 attached to the outer side of the bottom of the cleaning unit 7. The structures of the cleaning unit 7 and the blade 8 are described in detail below.

The cleaning unit 7 includes a main body 71 arranged at a position corresponding to the aspirating tube 1. Formed in the main body 71 are a through-hole 72 through which the aspirating tube 1 passes, a supply path 73 for supplying a cleaning liquid to the through-hole 72, and a discharge path 74 for discharging the cleaning liquid from the through-hole 72. The through-hole 72 is configured to pass vertically through the main body 71. The main body 71 if made of PPS (polyphenylene sulfide) resin. The cleaning unit 7 is configured so that cleaning liquid flows through the through-hole 72 and is discharged through the discharge path while cleaning liquid is supplied to the through-hole 72 from the supply path via a cleaning liquid supplying section which is not shown in the drawing.

The cleaning unit 7 is fixedly mounted in the vertical direction. Therefore, when aspirating blood from the sample container 110, and when discharging blood into the first chamber 21 and second chamber 22, the aspirating tube 1 is moved relative to the cleaning unit 7 by the vertical moving unit 5 moving the aspirating tube 1 vertically along the through-hole 72. As shown in FIG. 2, the cleaning unit 7 also is movable horizontally together with the aspirating tube 1 via the horizontal moving unit 6. The aspirating tube 1 aspirates blood at the aspirating position, and thereafter is cleaned by the cleaning unit 7 while being lifted by the vertical moving unit 5. The cleaned aspirating tube 1 then is moved horizontally toward the first discharging position or the second discharging position by the horizontal moving unit 6. At this time the cleaning unit 7 is also moved horizontally together with the aspirating tube 1 from the aspirating position toward the first discharging position or second discharging position via the horizontal moving unit 6. The aspirating tube 1 and the cleaning unit 7 are configured to move linearly between the aspirating position and the first discharging position and second discharging position via the horizontal moving unit in planar view.

The aspirating tube 1 discharges the blood at the first discharging position or second discharging position, and thereafter is cleaned by the cleaning unit 7 while being lifted by the vertical moving unit 5. The cleaned aspirating tube 1 is moved horizontally to the aspirating position together with the cleaning unit 7 by the horizontal moving unit 6.

Figure 4:
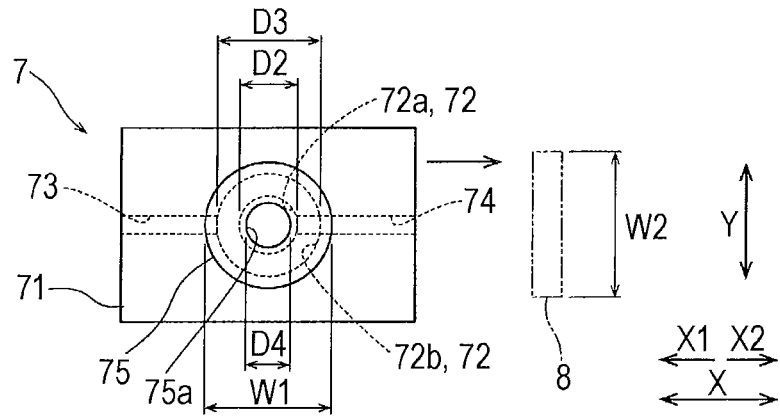
FIG. 4 illustrates the cleaning unit of FIG. 2 viewed from below.

The main body 71 incorporates a top hole part 72a that includes the through-hole 72 positioned in the top part (the part on the Z1 direction side) of the main body 71, and a bottom hole part 72b positioned in the bottom part (the part on the Z2 direction side) of the main body 71. As shown in FIGS. 3 and 4, the top hole part 72a is a part of the through-hole 72 which has a circular cross section with an internal diameter D2 (for example 1.7 mm) that is larger than the external diameter D1 (for example 1.5 mm) of the aspirating tube 1. The bottom hole part 72b is a part of the through-hole 72 which has a circular cross section with an internal diameter D3 (for example, 5 mm) that is larger than the internal diameter D2 of the top hole part 72a. As shown in FIG. 3, a tapered part 72c is provided between the top hole part 72a and the bottom hole part 72b, wherein the internal diameter gradually increases from the top hole part 72a toward the bottom hole part 72b. The supply path 73 which supplies cleaning liquid is configured to extend horizontally at a position corresponding to the bottom hole part 72b. The discharge path 74 which discharges cleaning liquid is configured to extend horizontally at a position corresponding to the top hole part 72a. According to this configuration, cleaning liquid supplied from the supply path 73 into the through-hole 72 circulates upward from the bottom hole part 72b and is discharged from the discharge path 74. The cleaning unit 7 employs this circulating flow to clean the aspirating tube 1 which is positioned within the through-hole 72.

As shown in FIG. 3, the cleaning unit 7 also has a diaphragm 75 for constructing the internal diameter of the through-hole 72 at the bottom end of the bottom hole part 72b. The diaphragm 75 is formed of PPS resin similar to the main body 71, and is fixedly mounted to the main body 71. As shown in FIGS. 3 and 4, the diaphragm 75 is configured with a through-hole 75a which has an internal diameter D4 (for example, 2 mm) that is larger than the internal diameter D2 of the top hole part 72a and smaller than the internal diameter of the bottom hole part 72b. Hence, the diaphragm 75 restricts the internal diameter of the through-hole 72 at the bottom end of the bottom hole part 72b so as to reduce the internal diameter more than the bottom hole part 72b, and increase the internal diameter more than the top hole part 72a. The diaphragm 75 at the part of the through-hole 75a has a circular cross section. The diaphragm 75 is configured as a peripheral portion having a predetermined thickness to circumscribe the through-hole 72 at the bottom end of the bottom hole part 72b. The diaphragm 75 also is configured to protrude downward (Z2 direction) from the main body 71 by a height H (for example, 8 mm). As shown in FIG. 4, the protruding part of the diaphragm 75 is circular in planar view, and has a width W1 (for example, 7 mm) which is greater than the internal diameter D3 of the bottom hole part 72b.

According to this configuration of the cleaning unit 7, when the aspirating tube is lifted with a substance 120 attached to the outer surface of the aspirating tube 1, some of the substance 120 is larger than the gap between the outer surface of the aspirating tube 1 and the inner surface of the through-hole 75 so that the substance 120 contacts the diaphragm 75 and adheres to the outer side of the protruding part of the diaphragm 75. The smaller substance and liquid attached to the outer surface of the aspirating tube 1 pass through the gap between the outer surface of the aspirating tube 1 and the inner surface of the through-hole 75 and are held in the through-hole 72, then removed by the cleaning liquid within the through-hole 72.

The blade 8 is configured to remove the substance 120 attached to the outer side of the protruding part of the diaphragm 75. That is, the blade 8 is configured to remove the substance 120 attached to the outside part near the bottom end of the bottom hole part 72b of the cleaning unit 7. The blade 8 is configured of elastically deformable plate-like silicone rubber to inhibit adherence of the substance. As shown in FIG. 4, the blade 8 has a width W2 (for example 10 mm) which is greater than the width W1 of the protruding part of the diaphragm 75. As shown in FIG. 2, the blade 8 is fixedly mounted to a metal plate member 9 attached at a position corresponding to the aspirating position.

After the cleaning unit 7 cleans the aspirating tube 1, the blade 8 is configured to remove the substance 120 attached to the outer part of the diaphragm 75 while the aspirating tube 1 is moved to the aspirating position or the discharge position by the horizontal moving unit 6. Specifically, the cleaning unit 7 moves relative to the blade 8 by the aspirating tube 1 and the cleaning unit 7 moving together toward the first discharging position or the second discharging position via the horizontal moving unit 6. The blade 8 is in a state of contact with the outer side of the protruding part of the diaphragm 75 at this time, as shown in FIG. 3. The blade 8 is configured to be elastically deformed when the cleaning unit 7 moves relative to the blade 8 while the blade 8 is in a state of contact with the outer side of the protruding part of the diaphragm 75. Thus, the substance 120 attached to the diaphragm 75 is removed by the blade 8. After the aspirating tube is cleaned by the cleaning unit 7, the blade 8 also removes the substance 120 attached to the outer side of the diaphragm 75 when the cleaning unit 7 moves relative to the blade 8 with the blade 8 in contact with the outer side of the protruding part of the diaphragm 75 even when the aspirating tube 1 and the cleaning unit 7 move from the first discharging position or the second discharging position toward the aspirating position.

The Blade 8 is arranged linearly between the aspirating position, first discharging position, and second discharging position in planar view. That is, the blade 8 is arranged on the moving path of the aspirating tube 1 and the cleaning unit 7 which are moved by the horizontal moving unit 6 in planar view. As shown in FIG. 3, the blade 8 is arranged at a position relative to which the cleaning unit moves while the blade 8 is in a state of contact with the protruding part of the diaphragm 75 without contacting the bottom surface 71*a* of the main body 71. Specifically, the blade 8 is arranged so that the position of the top end 81 is positioned between the bottom surface 71*a* of the main body 71 and the bottom surface 75*b* of the diaphragm 75 without contacting the cleaning unit 7.

The metal plate member 9 is fixedly attached at a position between the cleaning unit 7 and the sample container 110 at the aspirating position. The metal plate member 9 is configured to regulate the upward movement of the cap 110a of the sample container 110 when the aspirating tube 1 is lifted after aspirating blood at the aspirating position. Thus, the aspirating tube 1 is easily withdrawn from the cap 110a. The metal plate member 9 has a hole 91 which includes the through-hole through which the aspirating tube 1 passes. A dispersion prevention plate 92 is provided at the end of the metal plate member 9 on the opposite side from the side (the side in the X1 direction) on which the blade 8 is mounted to prevent airborne dispersion of the substance 120 removed by the blade 8 within the measuring unit 10.

Note that description of the second measuring unit 20 is omitted since the structure is identical to that of the first measuring unit 10.

As shown in FIG. 1, the sample transporting device 30 has the function of transporting the sample container 110 held in the rack 101 to predetermined positions of each measuring unit to transport the sample to the respective first measuring unit 10 and second measuring unit 20. Specifically, the sample transporting device 30 includes a pre-analysis rack holding unit 30a for holding a plurality of racks 101 which accommodate sample containers 110 containing unanalyzed samples, a post-analysis rack holding unit 30b for holding a plurality of racks 101 which accommodate sample containers 110 containing analyzed samples, and rack transporting unit 30c for moving the racks 101 in the X direction.

The control device 40 is configured by a personal computer (PC) and has the function of controlling the operations of both the first measuring unit 10 and the second measuring unit 20. The control device 40 is configured to analyze the components of the analysis object using detection results received from the first measuring unit 10 and second measuring unit 20 to obtain analysis results (red blood cell count, platelet count, hemoglobin concentration, white blood cell count and the like).

The operation of removing the substance 120 attached to the outer side of the bottom part of the cleaning unit 7 via the blade 8 in the blood analyzer 100 is described below with reference to FIGS. 2 and 3.

As shown in FIG. 2, the control device 40 lowers the aspirating tube 1 at the aspirating position via the vertical moving unit 5, and aspirates blood from the sample container 110. The aspirating tube 1 is inserted into the sample container 110 by piercing the cap 110a. After the aspirating tube 1 has aspirated the blood, the control device 40 lifts the aspirating tube 1 via the vertical moving unit 5. The control device 40 cleans the aspirating tube 1 via the cleaning unit 7 while the aspirating tube 1 is lifted. Thereafter, the control device 40 moves the cleaned aspirating tube 1 horizontally to the first discharging position corresponding to the first chamber 21 or the second discharging position corresponding to the second chamber 22 via the horizontal moving unit 6. As shown in FIG. 3, the blade 8 positioned on the moving path of the cleaning unit 7 comes into contact with the protruding part of the diaphragm 75 provided at the bottom part of the cleaning unit 7 via the movement of the cleaning unit 7 relative to the blade 8. The cleaning unit 7 moves horizontally relative to the blade 8 while the blade 8 is in a state of contact with the protruding part of the diaphragm 75. Thus, the substance 120 attached to the protruding part of the bottom part of the cleaning unit 7 is removed by the blade 8.

After the substance 120 on the bottom part of the cleaning unit 7 is removed, the control device 40 controls the aspirating tube 1 and the cleaning unit 7 to arrive at the first discharging position or the second discharging position via the horizontal moving unit 6. The aspirating tube 1 is lowered by the vertical moving unit 5, and discharges the blood to the corresponding first chamber 21 or the corresponding second chamber 22. After the blood has been discharged by the aspirating tube 1, the aspirating tube 1 is lifted by the vertical moving unit 5, and the aspirating tube 1 is cleaned by the cleaning unit 7. Thereafter, the control device 40 horizontally moves the cleaned aspirating tube 1 together with the cleaning unit 7 to the aspirating position via the horizontal moving unit 6. At this time the cleaning unit 7 moves in the horizontal direction relative to the blade 8 while the blade 8 is in a state of contact with the protruding part of the bottom part of the cleaning unit 7. Thus, the substance 120 attached to the protruding part of the bottom part of the cleaning unit 7 is removed by the blade 8.

The first embodiment provides a vertical moving unit 5 for moving the aspirating tube 1 relative to the cleaning unit 7 along the through-hole 72, and a blade 8 for removing a substance 120 attached to the outer side of the bottom part of the cleaning unit 7 when blood is aspirated by the aspirating tube 1. In this way when the aspirating tube 1 is moved relative to the cleaning unit 7 along the through-hole 72 by the vertical moving unit 5, the substance 120 attached to the outer side of the bottom part of the cleaning unit 7 is removed by the blade 8 even when the substance 120 (clots of blood, debris from the cap 110a and the like) attached to the outer surface of the aspirating tube 1 becomes attached to the outer side of the bottom part of the cleaning unit 7. As a result, a reduction in analysis accuracy caused by contamination of the measurement sample by the substance 120 attached to the cleaning unit 7 can be prevented by preventing contamination of the measurement sample by the substance 120 attached to the outer side of the bottom of the cleaning unit 7.

In the first embodiment, the blade 8 is configured to remove the substance 120 attached to the outer part of the through-hole 72 at the bottom end of the cleaning unit 7. In this way when the aspirating tube 1 is moved relative to the cleaning unit 7 along the through-hole 72 via the vertical moving unit 5, the substance 120 attached to the outer side of the bottom part of the cleaning unit 7 is effectively removed because the substance 120 attached to the outside surface of the aspirating tube 1 can be most easily removed by the blade 8 from the outside part of the bottom part of the cleaning unit 7.

In the first embodiment, a diaphragm 75 is provided on the outside part of the through-hole 72 at the bottom end of the cleaning unit 7 so as to protrude downward from the bottom surface 71a of the cleaning unit 7, and a blade 8 is configured to remove the substance 120 attached to the protruding part of the diaphragm 75. Therefore, the substance 120 is prevented from adhering to the outer side of the bottom part of the cleaning unit 7, that is, the parts other than the protruding part, when the substance 120 attached to the protruding part is removed by the blade 8 because a difference in level is formed relative to the bottom surface 71a of the cleaning unit 7 by the protruding part of the diaphragm 75. As a result, the substance 120 can easily be removed. Furthermore, an increase in the number of parts is avoided because the diaphragm 75 is diverted as the protruding part unlike when the diaphragm 75 and the protruding part are configured by separate members.

In the first embodiment, a horizontal moving unit 6 is provided to move the aspirating tube 1 together with the cleaning unit 7 from the aspirating position at which the blood sample is aspirated by the aspirating tube 1 toward the first and second discharging positions at which the blood is discharged by the aspirating tube 1, and the blade 8 is configured to remove the substance 120 from the outer side of the bottom part of the cleaning unit 7 after the aspirating tube 1 has been cleaned by the cleaning unit 7 and while the aspirating tube 1 is being moved to the first or second discharging position by the horizontal moving unit 6. Therefore, the substance 120 attached to the cleaning unit 7 is effectively prevented from contaminating the measurement sample at the first and second discharging positions because the aspirating tube 1 is delivered to the first or second discharging positions by the horizontal moving unit in a state in which the substance 120 attached to the outer side of the bottom part of the cleaning unit 7 has been removed by the blade 8.

In the first embodiment the blade 8 is configured to remove a substance 120 attached to the outside of the bottom part of the cleaning unit 7 by moving relative to the cleaning unit 7 while in a state of contact with the outer side of the bottom part of the cleaning unit 7. The blade 8 easily removes the substance 120 attached to the outside of the bottom part of the cleaning unit 7, thus easily preventing a reduction in the analysis accuracy caused by contamination of the measurement sample by the substance 120 attached to the cleaning unit 7.

In the first embodiment, the blade 8 is configured so that the cleaning unit 7 moves relative to the blade 8 while the blade 8 is in a state of contact with the outer side of the bottom part of the cleaning unit 7 when the aspirating tube 1 and the cleaning unit 7 are moved toward the first or second discharging position. In this way separate moving mechanisms to move the blade 8 relative to the cleaning unit 7 are unnecessary because the cleaning unit 7 moves relative to the blade 8 using the horizontal moving unit 6 to move the aspirating tube 1 and the cleaning unit 7 from the aspirating position to the first or second discharging position. As a result, contamination of the measurement sample by the substance 120 attached to the cleaning unit 7 is prevented while also avoiding an increase in the complexity of the apparatus structure.

In the first embodiment, the aspirating tube 1 and the cleaning unit 7 move linearly together between the aspirating position and the discharging positions via the horizontal moving unit 6 in planar view, and the blade 6 is arranged linearly between the aspirating position and the discharging positions in planar view. Therefore, in planar view, the a substance 120 attached to the outer side of the bottom part of the cleaning unit 7 is removed therefrom by the blade 8 on the moving path as the aspirating tube 1 and the cleaning unit 7 are moved from the aspirating position to a discharging position on the shortest path via the horizontal moving unit 6. As a result, an increase in the moving time of the aspirating tube 1 is prevented and contamination of the measurement sample by the substance 120 attached to the cleaning unit 7 is prevented because the path of the aspirating tube 1 from the aspirating position toward the discharging positions does not require a detour by the cleaning unit 7 for the purpose of removing the substance 120 therefrom.

In the first embodiment, the blade 8 is an elastically deformable plate-like member. Therefore, the substance 120 attached to the outer side of the bottom part of the cleaning unit 7 can be easily removed using the elastic deformation of this simply constructed blade 8.

In the first embodiment, a diaphragm 75 is provided at the outer side near the through-hole 72 at the bottom end of the cleaning unit 7 so as to protrude downward from the bottom surface of the cleaning unit 7, and the cleaning unit 7 is arranged at a position which is movable relative to the blade 8 while the blade 8 is in a state of contact with the protruding part of the diaphragm 75 without being in contact with the bottom surface 71*a* of the cleaning unit 7. Therefore, when the cleaning unit 7 moves relative to the blade 8, a substance 120 outside the protruding part of the diaphragm 75 is prevented from being moved on the outer side of the bottom part of the cleaning unit 7 by the blade 8. As a result, dispersal of the substance 120 on the outer side of the bottom part of the cleaning unit 7 is prevented.

In the first embodiment, the blade 8 is configured with a width W2 which is greater than the width W1 of the protruding part of the diaphragm 75. Therefore, when the cleaning unit 7 moves relative to the blade 8, the blade 8 contacts the entirety of the protruding part of the diaphragm 75 in the width direction. As a result, the blade 8 reliably removes the substance 120 attached to the protruding part of the diaphragm 75.

In the first embodiment, the blade 8 is configured to remove a substance 120 attached to the outer side of the diaphragm 75 which is provided near the through-hole 72 at the bottom end of the cleaning unit 7. Therefore, large size substance 120 is prevented from contaminating the measurement sample because the substance 120 that is larger than the gap between the outer surface of the aspirating tube 1 and the inner surface of the through-hole 75*a* which constricts the inner diameter of the diaphragm 75 adheres to the outer side of the diaphragm 75 and is removed by the blade 8. As a result, a reduction in analysis accuracy is prevented.

Second Embodiment

A blood analyzer 200 (refer to FIG. 1) of a second embodiment of the present invention is described below with reference to FIGS. 1, 2, and 5. Although a substance 120 attached to the outer side of the bottom part of the cleaning unit 7 is removed by a blade 8 in the first embodiment, the substance 120 attached to the outer side of bot the top part and the bottom part of the cleaning unit 7 is removed by air aspirated by an air suction unit 208 in the second embodiment.

Figure 5:
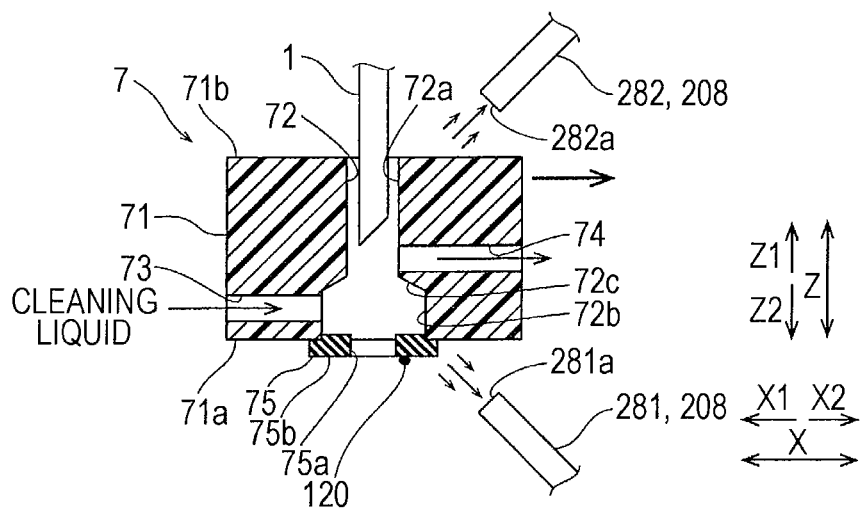
FIG. 5 is an enlarged cross sectional view of the cleaning unit and the air suction unit of the blood analyzer of the second embodiment.

As shown in FIG. 5, the blood analyzer 200 is provided with an air suction unit 208 for suctioning air using a negative pressure. The air suction unit 208 is configured to remove a substance 120 attached to the outer side of both the top part and the bottom part of the cleaning unit 7. Specifically, the air suction unit 208 includes a bottom pipe 281 which has an aspiration port 281*a* facing the bottom side of the cleaning unit 7, and a top pipe 282 which has an aspiration port 282*a* facing the top side of the cleaning unit 7. The bottom pipe 281 and the top pipe 282 are respectively configured to aspirate a substance 120 on the outer side of the bottom part and the top part of the cleaning unit 7. The bottom pipe 281 and the top pipe 282 are respectively inclined toward the bottom surface 71*a* and the top surface 71*b* of the main body 71 of the cleaning unit 7 in a direction (X2 direction) the aspirating tube 1 and the cleaning unit 7 face from the aspirating position to the first discharging position or second discharging position. That is, the bottom pipe 281 and the top pipe 282 are configured to aspirate toward the direction of movement side (X2 direction) when the aspirating tube 1 and the cleaning unit 7 move horizontally from the aspirating position to the first discharging position or second discharging position.

An air suction unit 208 is fixedly disposed within the measuring units 10 and 20. In this way the cleaning unit 7 moves relative to the air suction unit 208 when the horizontal moving unit 6 (refer to FIG. 2) moves the cleaning unit 7 horizontally from the aspirating position to either the first discharging position or the second discharging position, or from either the first discharging position or the second discharging position to the aspirating position. The blood analyzer 200 removes the substance 120 from the outer side of the bottom part and the top part of the cleaning unit 7 via the air suction unit 208 while the cleaning unit 7 is moved relative to the air suction unit 208. Therefore, the substance 120 can be removed by the air suction unit 208 from a larger area on the outer side of the bottom part and the top part of the cleaning unit 7. The bottom pipe 281 and the top pipe 282 of the air suction unit 208 are arranged on the movement path of the aspirating tube 1 and the cleaning unit 7 which are moved by the horizontal moving unit 6 as seen in planar view.

Figure 6:
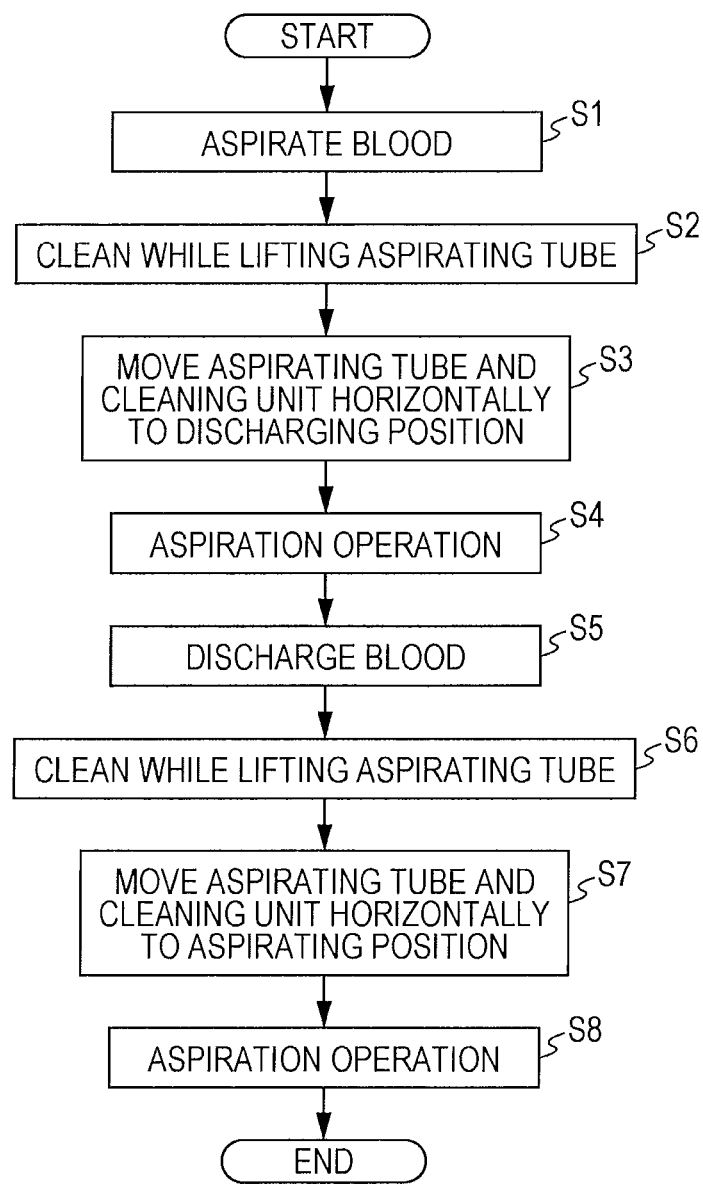
FIG. 6 is a flow chart illustrating the process performed by the control device when removing a substance in the blood analyzer of the second embodiment.

The process during substance removal by the control device 40 of the blood analyzer 200 is described below with reference to FIG. 6.

In step S1, the control device 40 lowers the aspirating tube 1 via the vertical moving unit 5 and aspirates the blood from the sample container 110. In step S2, the control device 40 cleans the aspirating tube 1 via the cleaning unit 7 while lifting the aspirating tube 1 via the vertical moving unit 5. After cleaning the aspirating tube 1, the control device 40 moves the aspirating tube 1 and the cleaning unit 7 together horizontally from the aspirating position to the first discharging position or the second discharging position via the horizontal moving unit 6 in step S3.

In step S4, the control device 40 starts the aspiration operation of the air suction unit 208 with a timing in which the cleaning unit 7 moves horizontally to a position corresponding to the bottom pipe 281 and the top pipe 282 of the air suction unit 208. The control device 40 continues the aspiration operation while the horizontal moving unit 6 moves the cleaning unit 7 relative to the air suction unit 208 until the cleaning unit 7 passes the air suction unit 208. Thus, the substance 120 attached to the outer side of the bottom part and the top part of the cleaning unit 7 is aspirated by the air suction unit 208. When the aspirating tube 1 and the cleaning unit 7 arrive at the first discharge position or the second discharge position, the control device 40 lowers the aspirating tube 1 via the vertical moving unit 5, and discharges the blood to the corresponding first chamber 21 or second chamber 22 in step S5. In step S6, the control device 40 cleans the aspirating tube 1 via the cleaning unit 7 while lifting the aspirating tube 1 via the vertical moving unit 5.

After cleaning the aspirating tube 1, the control device 40 moves the aspirating tube 1 and the cleaning unit 7 together horizontally from the first discharging position or the second discharging position to the aspirating position via the horizontal moving unit 6 in step S7. In step S8, the control device 40 starts the aspiration operation of the air suction unit 208 with a timing in which the cleaning unit 7 moves horizontally to a position corresponding to the bottom pipe 281 and the top pipe 282 of the air suction unit 208 similar to when the cleaning unit 7 moves toward the first discharging position or the second discharging position. The control device 40 continues the aspiration operation of the air suction unit 208 while the cleaning unit 7 moves relative to the air suction unit 208 until the cleaning unit 7 passes the air suction unit 208.

Note that other structures of the second embodiment are identical to those of the first embodiment.

The second embodiment provides an air suction unit 208 to remove a substance 120 by aspirating air. Thus, the substance 120 can be removed from the outer side of the bottom part and the top part of the cleaning unit 7 in a state of non-contact, that is, without the air suction unit 208 coming into contact with the cleaning unit 7.

In the second embodiment, the substance 120 attached to the outer side of the bottom part and the top part of the cleaning unit 7 is removed using the bottom pipe m281 and the top pipe 282 of the air suction unit 208. This configuration, therefore, prevents a reduction in analysis accuracy caused by contamination of the measurement sample by the substance 120.

The second embodiment also prevents a reduction in analysis accuracy caused by contamination of the measurement sample by the substance 120 attached to the cleaning unit 7 because the substance 120 attached to the outer side of the bottom part and the top part of the cleaning unit 7 is removed by the air suction unit 208 by providing the air suction unit 208 which removes the substance 120 attached to the outer side of the bottom part and the top part of the cleaning unit 7, and providing the vertical moving unit 5 which moves the aspirating tube 1 relative to the cleaning unit 7 along the through-hole 72 when the blood is aspirated by the aspirating tube 1.

Note that other effects of the second embodiment are identical to those of the first embodiment.

Note that the embodiment of the present disclosure is an example in all aspects and not to be considered limiting in any way. The scope of the present invention is expressed by the scope of the claims and not by the description of the embodiment, and includes all meanings and equivalences and modifications pertaining thereunto.

For example, although the specimen analyzing apparatus of the present invention is described by way of examples applied to blood analyzers for analyzing blood in the first and second embodiments, the present invention is not limited to these applications inasmuch as the specimen analyzing apparatus of the present invention is also applicable to analyzers other than blood analyzers such as, for example, urine analyzers for analyzing urine.

Although blood is aspirated from a sealed sample container 110 in the first and second embodiments, the present invention is not limited to this configuration. The present invention also may be configured to aspirate blood via an aspiration tube 1 from an open-type sample container which does not have a cap 110a. In this case the tip of the aspiration tube 1 need not be needle-like.

A substance attached to the outer side of the bottom part of the cleaning unit 7 is removed therefrom by a blade 8 provided below the cleaning unit 7 in the first embodiment, however, the present invention is not limited to this configuration. The present invention also may be configured with a blade provided above the cleaning unit 7 in addition to a blade provided below the cleaning unit 7 to remove a substance attached to the outer side of the top part and the bottom part of the cleaning unit 7.

In the first embodiment, a substance attached to the outer side of the bottom part of the cleaning unit 7 is removed therefrom through contact with a blade 8 on the outer side of the bottom part of the cleaning unit 7, however, the present invention is not limited to this configuration. The present invention also may be configured to remove a substance attached to the outer side of the bottom part of the cleaning unit 7 through contact with a cloth-like member on the outer side of the bottom part of the cleaning unit 7.

Figure 7:
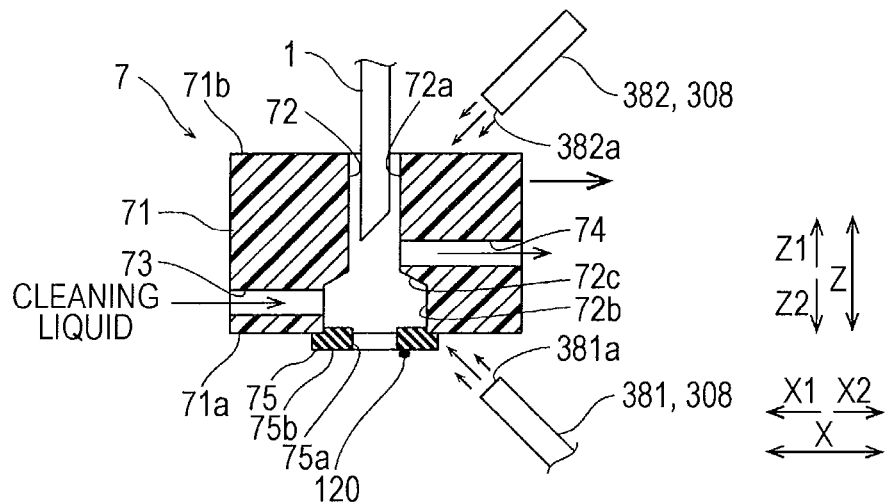
FIG. 7 shows a first modification of the second embodiment shown in FIG. 5.
Figure 8:
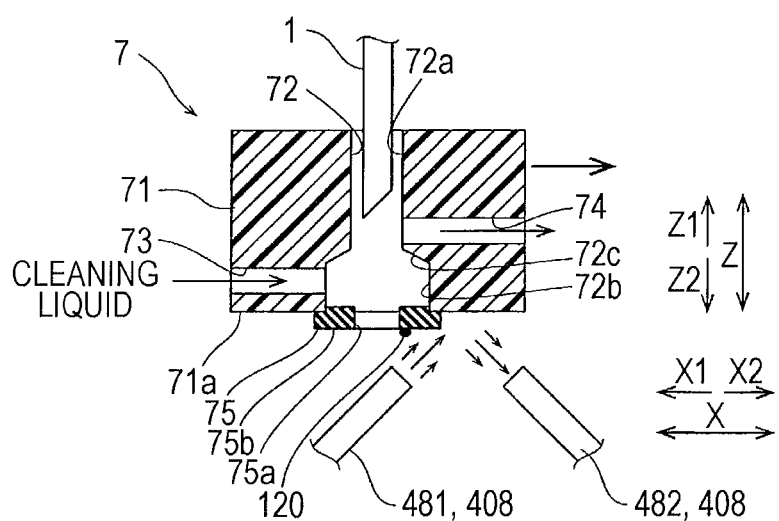
FIG. 8 shows a second modification of the second embodiment shown in FIG. 5.

Although a substance attached to the outer side of both the bottom part and the top part of the cleaning unit 7 is removed by air aspiration via an air suction unit 208 in the second embodiment, the present invention is not limited to this configuration. The present invention also may be configured to blow off a substance attached to the outer side of the bottom part and the top part of the cleaning unit by injecting air at the outer side of the bottom part and the top part of the cleaning unit 7 via an air injection unit 308 provided to inject air from a bottom pipe 381 and a top pipe 382 as in the first modification shown in FIG. 7. The present invention also may be configured to remove a substance attached to the outer side of the bottom of the cleaning unit by aspirating while injecting a cleaning liquid on the outer side of the bottom part of the cleaning unit 7 by providing a liquid washing unit 408 which has an injection pipe 481 to inject a washing liquid and an aspiration pipe 482 to aspirate the injected washing liquid as in the second modification shown in FIG. 8.

In the second embodiment, a substance attached to the outer side of the bottom part and the top part of the cleaning unit 7 is removed by providing a bottom pipe 281 and a top pipe 282 on both the bottom side and the top side of the cleaning unit 7, however, the present invention is not limited to this configuration. The present invention also may be configured to remove only a substance on the outer side of the bottom part of the cleaning unit 7 by providing a pipe to aspirate air only on the bottom side of the cleaning unit 7.

In the first and second embodiments, the cleaning unit 7 is moved relative to a blade 8 and an air suction unit 208 by moving the cleaning unit 7 horizontally via a horizontal moving unit 6 and fixedly mounting the blade 8 and air suction unit 208, respectively, however, the present invention is not limited to this configuration. The present invention also may be configured to move the blade 8 and the air suction unit 208 relative to the cleaning unit 7 by moving the blade 8 and the air suction unit 208. The present invention also may be configured to fixedly mount the air suction unit 208 relative to the cleaning unit 7 so that the air suction unit 208 and the cleaning unit 7 do not move relatively.

What is claimed is:

1. A specimen analyzing apparatus, comprising:
   an aspirating tube configured to aspirate a quantity of specimen from a specimen container;
   a detecting unit configured to analyze the quantity of specimen aspirated by the aspirating unit;
   a cleaning unit formed inside thereof with a through-hole dimensioned to allow the aspirating tube to pass therethrough inside the cleaning unit and a supplying path configured to supply a cleaning solution into the through-hole to wash the aspirating tube positioned in the through-hole inside the cleaning unit;
   a first moving unit configured to move the aspirating tube relative to the cleaning unit in such a manner that the aspirating tube reciprocates through the through-hole inside the cleaning unit; and
   a removing unit comprising a contact member movable relative to the cleaning unit, the contact member being configured to make sliding contact with an exterior of the cleaning unit to remove a substance attached on the exterior surface of the cleaning unit.

2. The specimen analyzing apparatus of claim 1, further comprising a second moving unit configured to move the cleaning unit relative to the removing unit.

3. The specimen analyzing apparatus of claim 1, wherein the contact member comprises an elastically deformable scraper configured to make sliding contact with the exterior of the cleaning unit to scrape the substance off the exterior surface of the cleaning unit.

4. The specimen analyzing apparatus of claim 2, wherein the second moving unit is configured to move the cleaning unit relative to the contact member being in contact with the exterior surface of the cleaning unit so that the contact member sweeps the exterior surface of the cleaning unit.

5. The specimen analyzing apparatus of claim 2, wherein the second moving unit is configured to move the cleaning unit, along with the aspirating tube, reciprocally between an aspirating position at which the aspirating tube aspirates the quantity of specimen, and a discharging position at which the aspirating tube discharges the quantity of aspirated specimen.

6. The specimen analyzing apparatus of claim 5, wherein the second moving unit is configured to move the aspirating tube and the cleaning unit together along a linear line running between the aspirating position and the discharging position in a planar view; and
   the contact member is arranged in a stationary manner at a location in the linear line in the planar view.

7. The specimen analyzing apparatus of claim 5, wherein the contact member is positioned relative to the cleaning unit to sweep the exterior surface of the cleaning unit while the cleaning unit being moved between the aspirating position and the discharging position by the second moving unit.

8. The specimen analyzing apparatus of claim 2, wherein the through-hole is formed to pass through inside the cleaning unit in a vertical direction;
   the first moving unit is configured to move the aspirating tube through the through-hole inside the cleaning unit in the vertical direction; and
   the second moving unit is configured to move the cleaning unit horizontally relative to the removing unit.

9. The specimen analyzing apparatus of claim 8, wherein the cleaning unit comprises a plate of a predetermined thickness arranged to form at least a part of the lower surface of the cleaning unit, the plate being formed with a hole coaxially with the through-hole of the cleaning unit so that the hole of the plate forms a lower end portion of the through-hole, and the aspirating tube moves through the hole of the plate; and
   the hole of the plate is dimensioned to trap the substance by a lower surface of the plate, and the removing unit is configured to remove the substance trapped on the lower surface of the plate.

10. The specimen analyzing apparatus of claim 9, wherein the contact member is configured to make sliding contact with the plate.

11. The specimen analyzing apparatus of claim 10, wherein the contact member has a width in a direction perpendicular to a direction in which the second moving unit moves the cleaning unit relative to the removing unit, the width of the contact member being greater than a width of the plate measured in the same perpendicular direction.

12. The specimen analyzing apparatus of claim 8, wherein the cleaning unit comprises a diaphragm arranged to form at least a part of the lower surface of the cleaning unit and formed with a hole coaxially with the through-hole of the cleaning unit so that the hole of the diaphragm forms a lower end portion of the through-hole, and the aspirating tube moves through the hole of the diaphragm, a diameter of the through-hole being reduced at the diaphragm
   to trap the substance by a lower surface of the diaphragm, and the removing unit is configured to remove the substance trapped on the lower surface of the diaphragm.

13. The specimen analyzing apparatus of claim 8, wherein the removing unit is positioned lower than the cleaning unit to remove the substance attached on a lower surface of the cleaning unit.

14. The specimen analyzing apparatus of claim 8, wherein the removing unit is positioned higher than the cleaning unit to remove the substance attached on an upper surface of the cleaning unit.

15. The specimen analyzing apparatus of claim 13, wherein the removing unit is positioned relative to the cleaning unit to remove the substance attached near the through-hole in the lower surface of the cleaning unit.

16. A specimen analyzing apparatus, comprising:
   an aspirating tube configured to aspirate a quantity of specimen from a specimen container;
   a detecting unit configured to analyze the quantity specimen aspirated by the aspirating unit;
   a cleaning unit formed inside thereof with a through-hole dimensioned to allow the aspirating tube to pass therethrough inside the cleaning unit and a supplying path configured to supply a cleaning solution into the through-hole to wash the aspirating tube positioned in the through-hole inside the cleaning unit;
   a first moving unit configured to move the aspirating tube relative to the cleaning unit reciprocally through the through-hole inside the cleaning unit; and
   means for removing a substance attached on an exterior surface of the cleaning unit.

17. A specimen analyzing method comprising:
- aspirating a quantity of specimen from a specimen container by an aspirating tube;
- washing the aspirating tube inside a cleaning unit that is formed inside thereof with a through-hole dimensioned to allow the aspirating tube to pass therethrough inside the cleaning unit and a supplying path configured to supply a cleaning solution into the through-hole to clean the aspirating tube positioned in the through-hole inside the cleaning unit;
- moving the cleaning unit reciprocally between an aspirating position at which the aspirating tube aspirates the quantity of specimen, and a discharging position at which the aspirating tube discharges the quantity of aspirated specimen; and
- making sliding contact with an exterior surface of the cleaning unit to remove a substance attached on the exterior surface of the cleaning unit while moving the cleaning unit between the aspirating position and the discharging position.

* * * * *